United States Patent [19]

Hoppstock et al.

[11] 4,108,919

[45] Aug. 22, 1978

[54] OXIDATIVE DEHYDROGENATION OF OLEFINS TO DIOLEFINS

[75] Inventors: Frederic H. Hoppstock, Massillon; Kenneth J. Frech, Tallmadge, both of Ohio

[73] Assignee: The Goodyear Tire & Rubber Company, Akron, Ohio

[21] Appl. No.: 779,218

[22] Filed: Mar. 18, 1977

Related U.S. Application Data

[63] Continuation-in-part of Ser. No. 614,383, Sep. 18, 1975, abandoned.

[51] Int. Cl.² ............................................. C07C 11/12
[52] U.S. Cl. .............................. 260/680 E; 260/680 D
[58] Field of Search .................... 260/680 E, 680 D

[56] References Cited

U.S. PATENT DOCUMENTS

| | | | |
|---|---|---|---|
| 3,825,502 | 7/1974 | Takenaka et al. | 260/680 E |
| 3,862,256 | 1/1975 | Isailingold et al. | 260/680 E |
| 3,903,189 | 9/1975 | Hoppstock et al. | 260/680 E |
| 3,917,736 | 11/1975 | Frech et al. | 260/680 E |
| 3,932,551 | 1/1976 | Grasselli et al. | 260/680 E |
| 3,956,181 | 5/1976 | Grasselli et al. | 260/680 E |
| 4,002,696 | 1/1977 | Hoppstock | 260/680 E |

*Primary Examiner*—Helen M. S. Sneed
*Attorney, Agent, or Firm*—J. Y. Clowney

[57] ABSTRACT

There is disclosed a method comprising the oxidative dehydrogenation of at least one hydrocarbon selected from the group consisting of butene-1, butene-2, 2-methyl-1-butene, 2-methyl-2-butene, 3-methyl-1-butene, n-pentene, 2,3-dimethyl-1-butene, 2,3-dimethyl-2-butene, 2-methyl-1-pentene, 2-methyl-2-pentene, 4-methyl-2-pentene, 3-methyl-1-pentene, 3-methyl-2-pentene, 2-ethyl-1-butene, ethyl benzene and isopropyl benzene at oxidative dehydrogenation conditions while in contact with a catalyst consisting essentially of a mixture of zinc and molybdenum in combination with oxygen which is activated with chromium in combination with oxygen, said catalyst being calcined for at least 1 hour at 400° C. to 1100° C. prior to use.

10 Claims, No Drawings

OXIDATIVE DEHYDROGENATION OF OLEFINS TO DIOLEFINS

This application is a continuation-in-part of application Ser. No. 614,383, filed Sept. 18, 1975, now abandoned.

This application is directed to a process of the oxidative dehydrogenation of hydrocarbons.

For instance, employing the process of this invention, butene-1 and/or butene-2 can be oxidatively dehydrogenated to butadiene, isoamylenes such as 2-methyl-1-butene, 2-methyl-2-butene and 3-methyl-1-butene to isoprene, n-pentenes to piperylene, 2,3-dimethyl-1- or 2-butenes to 2,3-dimethyl-1,3-butadiene, methyl pentenes such as 2-methyl-1-pentene, 2-methyl-2-pentene, 4-methyl-2-pentene, 3-methyl-1-pentene, 3-methyl-2-pentene and 2-ethyl-1-butene to methyl pentadienes, ethyl benzene to styrene and isopropyl benzene to α-methyl styrene.

The invention provides an oxidative dehydrogenation process which reduces or eliminates endothermic heat requirements, permits continuous burn-off of carbon from the catalyst, permits longer catalyst life, provides higher per pass conversions and higher yields or selectivity to the desired products. The process also allows the direct efficient conversion of 1-olefins to diolefins, usually only 2-olefins are readily converted to diolefins. Thus, the process of this invention is somewhat of an improvement over those of the prior art.

According to the invention, hydrocarbons are oxidatively dehydrogenated by subjecting at least one hydrocarbon selected from the group consisting of butene-1, butene-2, 2-methyl-1-butene, 2-methyl-2-butene, 3-methyl-1-butene, n-pentene, 2,3-dimethyl-1-butene, 2,3-dimethyl-2-butene, 2-methyl-1-pentene, 2-methyl-2-pentene, 4-methyl-2-pentene, 3-methyl-1-pentene, 3-methyl-2-pentene, 2-ethyl-1-butene, ethylbenzene and isopropyl benzene to oxidative dehydrogenation conditions while in the presence of a catalyst comprising a mixture of cobalt and molybdenum in combination with oxygen and/or zinc and molybdenum in combination with oxygen which is activated with chromium in combination with oxygen, said catalyst being calcined for at least 1 hour at 400° C to 1100° C prior to use.

It has been discovered that if the catalyst mixture is treated with a modifier such as an alkali metal oxide or hydroxide or an alkaline earth oxide or hydroxide in amounts so that the modifier shall range from 0.1 to 5 weight percent calculated as the oxide of the alkali or alkaline earth metal based on the weight of the other catalyst components prior to its being finally calcined, the activity of the catalyst is enhanced somewhat.

The catalyst of this invention can be employed with good success without the use of a support. However, it is believed that the catalyst of this invention is best employed by impregnating the mixture of catalyst components on a support. Examples of such useful support materials are alumina, silica-alumina, silicon, silicon carbide, pumice and the like. Of these, it is preferred to utilize alumina as the support material. When a support is employed for the catalyst, the amounts of catalyst components impregnated on the support should range from about 1 to about 25 weight percent, with from about 15 to about 20 weight percent being more preferred, calculated as cobalt molybdate and/or zinc molybdate. The amount of chromium impregnated should range from about 1.5 to about 40 weight percent calculated as chromium trioxide, with 12 to about 27 weight percent being more preferred.

The relationship of the chromium calculated as chromium trioxide to the cobalt and molybdenum and/or zinc and molybdenum employed may be expressed as the ratio of the atomic weight of chromium to the atomic weight of the total of the cobalt and molybdenum and/or zinc molybdenum (Cr/CoMo or Cr/ZnMo). Thus, the Cr/CoMo or Cr/ZnMo should range from 0.1/1 to 5/1 with from 0.25/1 to 4/1 being more preferred and 0.5/1 to 3/1 being most preferred. On the other hand, good results have been obtained when the loadings on the support are approximately equal weight ratios of the chromium as chromium trioxide to the cobalt, zinc and molybdenum calculated as $CoMoO_4$ or $ZnMoO_4$.

The catalyst of the invention can be prepared by conventional techniques. The preferred techniques are to use the available $CoMoO_4$ and $ZnMoO_4$. To prepare the catalyst, one needs only to dissolve the cobalt or zinc molybdate in a slightly acidified water solution, for instance, 15–20 percent by weight HCl, and impregnate the desired support with sufficient amounts of such solution to impart the desired residual amount calculated as $CoMoO_4$ or $ZnMoO_4$, dry this mixture. Then dissolve the water soluble chromium trioxide, $CrO_3$, also commercially available, and impregnate the support with sufficient $CrO_3$ to give the desired amount of chromium calculated as $CrO_3$. These impregnations can be conducted in any order. It has been found that either catalyst component can be impregnated onto the support and dried or calcined between impregnations. On the other hand, the catalysts of the invention may be prepared by other techniques using the salts of cobalt, zinc, molybdenum and chromium in the proper amounts to give the desired amounts in the finished catalysts. Representative of these salts are nitrates, halides, oxyhalides and oxalates. The oxides of these metals may also be used in some cases. These techniques are known to those skilled in the art.

If it is desired to use alkali metal or alkaline earth metal oxides, a convenient method is to utilize a water solution of the hydroxide and impregnate the support with a sufficient amount to give the desired amount of alkali metal or alkaline earth metal oxide after calcining. After the catalyst components have been impregnated on the support, the catalyst may be allowed to dry and is calcined or calcined wet for at least 1 hour or more at temperatures ranging from about 400° to about 600° C.

It has been discovered however that the activity of the catalyst is greatly enhanced if there is an additional calcining treatment at temperatures between about 750° C and 1100° C for at least 1 hour prior to use as an oxidative dehydrogenation catalyst. There seems to be no upper limit as to the time which the catalyst can be calcined. Successful catalysts have been prepared which were calcined as long as 72 hours.

All of the foregoing is not to say that the catalyst cannot be employed without the use of a support.

It is usually conventional in a heterogeneous catalyst process such as that of this invention to employ continuous reaction systems either using fixed beds or fluidized beds. Therefore, it is usually preferred to employ the catalysts of this invention in a form which will not crush or become pulverized readily. For that reason, it is usually more satisfactory to impregnate the catalyst onto a suitable rugged support, such as those mentioned previously.

The oxidative dehydrogenation process of this invention can be conducted under fairly reasonable reaction conditions. For instance, the temperatures employed may vary from about 350° C to 650° C with 450° C to 575° C being more preferred.

In order to provide a better temperature control of the process, it is usually desirable to employ a diluent, but a diluent is not absolutely required. Materials such as steam, nitrogen, methane, hydrogen, carbon dioxide or other diluents known to be stable under the reaction conditions may be employed. Steam is preferred. When a diluent is employed, the diluent to hydrocarbon mole ratio may be from 1/1 to 20/1 with a more preferred range of 2/1 to 5/1.

While oxygen may be used as an oxidant, it is more economical and usually preferred to employ air as the oxidant. The oxidant mole ratio to the hydrocarbon feed in terms of $O_2/HC$ should be between 0.1/1 and 10/1 with a more preferred range being 0.5/1 to 5/1.

The rate at which the hydrocarbon is passed through the reactor and is in contact with the catalyst is the Liquid Hour Space Velocity (LHSV) and is defined as the volume of hydrocarbon as a liquid passed over a given volume of catalyst per hour. The LHSV employed in this invention should range from about 0.1 to about 100 with a more preferred LHSV of 0.5 to 10 being employed.

One particularly interesting embodiment of this process is the preparation of 2,3-dimethyl-1,3-butadiene by the oxidative dehydrogenation of 2,3-dimethyl-2-butene and/or 2,3-dimethyl-1-butene, particularly mixtures where the 2-olefin is in the range of from about 65 to 80 mole percent.

The invention is further illustrated by reference to the following examples which are intended to be representative rather than restrictive of the scope.

In the examples, a stainless steel tube of 0.43 inches internal diameter was used as a reactor. In this reactor there was placed 6 cubic centimeters (cc) of the particular catalyst employed. The reactor was heated in a tubular furnace and temperature controlled by means of thermocouples placed at various locations. The hydrocarbon feed and the water diluent were introduced as liquids using syringe infusion pumps. The air, used as an oxidant, was metered into the system. The reactor effluent was analyzed using gas chromatographic techniques. All percentages are reported by weight except as noted.

EXAMPLE I

In this experiment, run 1 is considered to be a control and the catalyst was prepared by impregnating 30 grams of alumina (8 to 16 mesh which had been dried at 900° C with 0.3 g of KOH dissolved in 15 cc of water) followed by calcination for 1 hour at 520° C. Then 4.5 grams of $CoMoO_4$ dissolved in 15 cc of 18 weight percent HCl was added to the alumina and calcined for 1 hour at 400° C. Prior to use, the catalyst was calcined for approximately 1 hour at 940° C. The catalyst thus calculates to be 15 weight percent $CoMoO_4$ plus 0.5 weight percent $K_2O$.

The catalyst employed in run 2 was prepared by impregnating 10 grams of a commercial catalyst containing 19 percent $Cr_2O_3$ on alumina which had been calcined for approximately 1 hour at 600° C with 0.1 gram of KOH dissolved in 5 cc of water followed by calcination at 600° C for approximately 1 hour, then 1.5 grams of $CoMoO_4$ dissolved in 18 weight percent HCl solution was added to this mixture followed by calcining at 600° C for approximately 1 hour. Prior to use, the catalyst was calcined for approximately 1 hour at 940° C. The finished catalyst calculates to be 19 percent $Cr_2O_3$ plus 0.5 $K_2O$ plus 15 percent $CoMoO_4$ on alumina, all percentages in weight percent. Run 2 is considered representative of the invention. 2,3-Dimethyl-2-butene was used as the feed at an LHSV of 0.5 at 525° C. The results and some operating conditions are given in Table 1 below. Col 1 is the run number, Col 2 is the conversion of the 2,3-dimethyl-2-butene (DMB2) in mole percent, Col 3 is the selectivity to 2,3-dimethylbutadiene (DMBD), Col 4 is the mole ratio of water (used as a diluent) to the hydrocarbon feed, Col 5 is the ratio of air to hydrocarbon feed calculated as the mole ratio of oxygen to DMB2.

TABLE 1

| 1 | 2 | 3 | 4 | 5 |
|---|---|---|---|---|
| Run 1 | 64 | 82 | 4.0 | 1.3 |
| Run 2 | 76 | 81 | 3.2 | 1.3 |

EXAMPLE II

In this experiment, run 1 is considered a control and run 2 is considered representative of the invention. In these experiments, the catalysts were prepared as in Example I. The difference between Example I and Example II is that 2,3-dimethyl-1-butene (DMB1) was employed as the olefin to be oxydehydrogenated instead of 2,3-dimethyl-2-butene. In Table 2, Col 1 is the olefin oxydehydrogenated, Col 2 is the conversion of the DMB1 in mole percent, Col 3 is the selectivity to the corresponding diolefin, DMBD, in mole percent, Col 4 is the mole ratio of the diluent, ($H_2O$ or steam), to the feed, Col 5 is the mole ratio of the oxidant to feed (air), calculated as mole ratio of $O_2$ to feed.

TABLE 2

| 1 | 2 | 3 | 4 | 5 |
|---|---|---|---|---|
| DMB1 | 50 | 68 | 3.7 | 1.4 |
| DMB1 | 64 | 76 | 3.0 | 1.3 |

EXAMPLE III

In these experiments, run 1 is considered to be a control and the catalyst there employed was prepared by drying 10 grams of $Al_2O_3$ at 400° C and impregnating this alumina with 0.1 gram of KOH dissolved in 5 cc water followed by calcining at 400° C for 1 hour. Then 1.5 grams $CoMoO_4$ dissolved in 5 cc of 18 weight percent HCl was added and calcined at 918° C for approximately 1 hour.

The catalyst employed in run 2 which represents the practice of the invention was prepared by drying 100 grams of a commercial catalyst consisting of 19 weight percent $Cr_2O_3$ on alumina at 600° C followed by 1 gram of KOH dissolved in 25 cc water and calcining at 600° C for approximately 1 hour. Then 15 grams of $CoMoO_4$ dissolved in 25 cc of 18 weight percent HCl solution was added and dried at 600° C. The catalyst received a final calcining at 940° C for approximately 1 hour prior to use.

In these runs, 2-methyl-2-butene (2MB2) was employed as the olefin oxydehydrogenated at an LHSV of 0.5 and the temperature was maintained at 525° C. In Table 3, Col 1 is the olefin, Col 2 is the conversion of the olefin in mole percent, Col 3 is the selectivity to the corresponding diolefin, isoprene, in mole percent, Col 4 is the mole ratio of the diluent (water) to the feed, Col 5 is the mole ratio of the oxidant (air) to the feed calculated as the mole ratio of $O_2$.

TABLE 3

| 1 | 2 | 3 | 4 | 5 |
|---|---|---|---|---|
| 2MB2 | 29 | 45 | 3.0 | 1.0 |
| 2MB2 | 19 | 69 | 2.3 | 1.0 |

EXAMPLE IV

In this example, all the runs were conducted with a feed which was 2,3-dimethyl-2-butene at an LHSV of 0.5 at two different temperatures which are listed in Table 4. In run 1, the catalyst employed was 19 weight percent $Cr_2O_3$ on alumina which had been calcined at 950° C., and is a control. Run 2 catalyst was prepared by impregnating 10 grams of alumina with 1.5 grams of $CoMoO_4$ dissolved in 5 cc of 18 weight percent HCl solution which was calcined at 940° C for 1 hour, and is a control. Run 3 the catalyst was prepared by impregnating 20 grams of a commercial catalyst which was 19 percent $Cr_2O_3$ on alumina with 3 grams of $CoMoO_4$ and calcining the catalyst at 625° C for approximately 1 hour. The catalyst received a final calcination prior to use at 960° C for approximately 1 hour, thus is representative of the invention. Run 4 the catalyst was the same as the catalyst in run 2 except it contained 0.5 weight percent $K_2O$, and is a control. In run 5 the catalyst was prepared by impregnating 10 grams of 19 weight percent $Cr_2O_3$ on alumina with 0.1 gram of KOH in 2.5 cc of water calcined at 600° C for 1 hour, then 1.5 gram $CoMoO_4$ in 2.5 cc 18 percent HCl solution was added. The catalyst was calcined for 1 hour at 600° C. The catalyst received a final calcination at 940° C for 1 hour. Thus, runs 1, 2 and 4 are considered controls and runs 3 and 5 represent the invention. In run 6 the catalyst was prepared 20 grams of 19 percent by weight $Cr_2O_3$ on alumina with 3 grams of $CoMoO_4$ and calcining the catalyst for 1 hour at 625° C. The catalyst received a final calcining at 960° C for approximately 1 hour prior to use. The catalyst employed in run 7 is identical to that of run 6 except that it contained 0.1 weight percent $K_2O$ and the catalyst received a final calcining of 800° C for a period of 16 hours. In run 8 the catalyst employed was approximately the same as that employed in run 6 except it contained 0.5 weight percent $K_2O$. Thus runs 6 and 8 represent the invention. In Table 4, the results and some operating conditions are given. Col 1 is run number, Col 2 is temperature, Col 3 is the conversion of the 2,3-dimethyl-2-butene in mole percent, Col 4 is the selectivity to 2,3-dimethylbutadiene in mole percent, Col 5 is the mole ratio of the water to feed and Col 6 is the mole ratio of air to feed calculated as $O_2$.

TABLE 4

| 1 | 2 | 3 | 4 | 5 | 6 |
|---|---|---|---|---|---|
| 1 | 525 | 37 | 56 | 3.3 | 1.2 |
| 2 | 525 | 59 | 74 | 3.3 | 1.2 |
| 3 | 525 | 75 | 72 | 2.9 | 1.6 |
| 4 | 525 | 57 | 72 | 3.2 | 1.2 |
| 5 | 525 | 64 | 76 | 3.0 | 1.3 |
| 6 | 450 | 75 | 79 | 3.2 | 1.3 |
| 7 | 450 | 42 | 71 | 4.0 | 1.7 |
| 8 | 450 | 49 | 86 | 2.9 | 1.4 |

EXAMPLE V

In these experiments, 2,3-dimethyl-2-butene was oxidatively dehydrogenated with the same catalyst at several different temperatures at an LHSV of 0.5. The catalyst employed was prepared by impregnating 0.1 gram of KOH onto 10 grams of 19 weight percent $Cr_2O_3$ on alumina and heating to 600° C for approximately 1 hour. Then 1.5 grams of $CoMoO_4$ was impregnated onto the catalyst and heated for 1 hour at 600° C. The catalyst received a final calcining of 940° C. for 1 hour prior to use. The results and some operating conditions are reported in Table 5, in which Col 1 identifies the catalysts, Col 2 the temperature in ° C, Col 3 the conversion of DMB2 in mole percent, Col 4 the selectivity to DMBD in mole percent, Col 5 the mole ratio steam to DMB2 and Col 6 the $O_2$ to DMB2 mole ratio.

TABLE 5

| 1 | 2 | 3 | 4 | 5 | 6 |
|---|---|---|---|---|---|
| A | 525 | 64 | 76 | 3.0 | 1.3 |
| A | 500 | 64 | 80 | 3.2 | 1.3 |
| A | 475 | 50 | 83 | 3.0 | 1.2 |
| A | 450 | 36 | 91 | 3.1 | 1.3 |

EXAMPLE VI

This example illustrates the use of a non-supported catalyst. The catalyst employed in run 1 was 10 grams of $CoMoO_4$ to which was added 3.2 grams of $CrO_3$ in 5 cc of water and calcined at 640° C. The catalyst employed in run 2 was identical to run 1 except that it was recalcined at 940° C for approximately 1 hour just prior to use. 2,3-dimethyl-2-butene was dehydrogenated at an LHSV of 0.5 at 450° C. Col 1 is the mole percent conversion of the 2-methyl-butene-2, Col 2 is the selectivity to 2,3-dimethyl butadiene, Col 3 is the water to hydrocarbon ratio and Col 4 is the $O_2$ to hydrocarbon ratio employed.

TABLE 6

| 1 | 2 | 3 | 4 |
|---|---|---|---|
| 76 | 78 | 3.7 | 1.7 |
| 79 | 80 | 4.1 | 2.1 |

EXAMPLE VII

In this example, all runs were made using 2,3-dimethyl-2-butene as the feed at an LHSV of 0.5. In runs 2 and 3, the catalyst was prepared by drying 10 grams of $Al_2O_3$, impregnating 3.2 grams of $CrCO_3$ dissolved in 5 cc of water, followed by calcining at 640° C, then 0.1 gram of KOH dissolved in 5 cc water was added followed by calcining at 640° C, then 1 gram of $ZnMoO_4$ dissolved in 5 cc of 18 weight percent HCl was added, followed by calcining at 640° C. The two additions of $ZnMoO_4$ was made because of the solubility problem with $ZnMoO_4$. The catalyst received a final calcination at 980° C for 1 hour prior to use.

The catalyst employed in runs 2 and 4 were prepared in the same nature as the catalyst of runs 1 and 3 except that the final addition of $ZnMoO_4$ was 1.5 gram instead of 1.0 gram.

The results and operating conditions are given in Table 7 below in which Col 1 is the run number, Col 2 is the oxidative dehydrogenation temperature, Col 3 is the conversion of DMB2, Col 4 is the selectivity to DMBD, Col 5 is the $H_2O$/HC mole ratio, Col 6 is the $O_2$/HC mole ratio.

TABLE 7

| 1 | 2 | 3 | 4 | 5 | 6 |
|---|---|---|---|---|---|
| 1 | 525 | 81 | 77 | 3.4 | 1.6 |
| 2 | 525 | 80 | 77 | 4.4 | 1.5 |
| 3 | 450 | 61 | 83 | 3.9 | 1.8 |
| 4 | 450 | 71 | 82 | 4.1 | 1.8 |

Thus, the examples set forth above indicate an improvement in the chrome modification of catalysts comprising zinc molybdate and cobalt molybdate, and optionally some alkali metal oxides may also be included.

While certain representative embodiments and details have been shown for the purpose of illustrating the invention, it will be apparent to those skilled in this art that various changes and modifications may be made therein without departing from the spirit or scope of the invention.

What is claimed is:

1. A process of oxidative dehydrogenation which comprises subjecting at least one hydrocarbon from the group of butene-1, butene-2, 2-methyl-1-butene, 2-methyl-2-butene, 3-methyl-1-butene, n-pentene, 2,3-dimethyl-1-butene, 2,3-dimethyl-2-butene, 2-methyl-1-pentene, 2-methyl-2-pentene, 4-methyl-2-pentene, 3-methyl-1-pentene, 3-methyl-2-pentene and 3-ethyl-1-butene to oxidative dehydrogenation conditions while said hydrocarbons are in the presence of a catalyst consisting essentially of a mixture of zinc molybdate ($ZnMoO_4$) and at least one of chromium oxide ($CrO_3$ or $Cr_2O_3$), said catalyst mixture being calcined for at least 1 hour at 400° to 1100° C. prior to use, in which the relationship of the chromium to zinc and molybdenum expressed as the atomic ratio of chromium (Cr) to the total of the zinc and molybdenum (ZnMo) ranges from about 0.1/1 to about 5/1.

2. The process according to claim 1 in which the catalyst is impregnated on a support.

3. The process according to claim 2 in which the amount of catalyst impregnated on the support ranges from about 1.5 to about 40 weight percent of chromium calculated as $CrO_3$ and the amount of zinc and molybdenum calculated as zinc molybdate ranges from about 1 to about 25 weight percent.

4. The process according to claim 3 in which the support is alumina.

5. The process according to claim 1 in which water is employed as a diluent.

6. The process according to claim 1 in which the hydrocarbon is selected from the group of 2,3-dimethyl-1-butene and/or 2,3-dimethyl-2-butene.

7. The process according to claim 1 in which air is employed as an oxidant in amounts to provide an oxygen/hydrocarbon mole ratio of 0.5/1 to 5/1.

8. The process according to claim 1 in which the air is employed as an oxidant in amounts to provide an oxygen/hydrocarbon mole ratio of 0.5/1 to 5/1 and in which the catalyst is impregnated on an alumina support in amounts ranging from about 12 to about 27 weight percent by weight of $CrO_3$ and from about 15 to about 20 weight percent of $ZnMoO_4$ by weight of alumina as the support and in which water is employed as a diluent in amounts to give a mole ratio of diluent/hydrocarbon of about 2/1 to about 5/1.

9. The process according to claim 8 in which the hydrocarbon is 2,3-dimethyl-1-butene and/or 2,3-dimethyl-2-butene.

10. The process according to claim 1 in which the catalyst is treated with a modifier comprising an alkali metal oxide or hydroxide or an alkaline earth metal oxide or hydroxide in amounts ranging from 0.1 to 5 weight percent based on the weight of the other catalyst components.

* * * * *